US00RE50422E

(19) United States
(12) Reissued Patent
Renstad et al.

(10) Patent Number: US RE50,422 E
(45) **Date of Reissued Patent: *May 13, 2025**

(54) MEDICAMENT DELIVERY DEVICE

(71) Applicant: SHL MEDICAL AG, Zug (CH)

(72) Inventors: Rasmus Renstad, Stockholm (SE); Daniel Säll, Segeltorp (SE)

(73) Assignee: SHL Medical AG, Zug (CH)

( * ) Notice: This patent is subject to a terminal disclaimer.

(21) Appl. No.: 18/117,861

(22) Filed: Mar. 6, 2023

Related U.S. Patent Documents

Reissue of:
(64) Patent No.: 10,512,724
Issued: Dec. 24, 2019
Appl. No.: 15/523,589
PCT Filed: Oct. 22, 2015
PCT No.: PCT/EP2015/074463
§ 371 (c)(1),
(2) Date: May 1, 2017
PCT Pub. No.: WO2016/078863
PCT Pub. Date: May 26, 2016

U.S. Applications:
(63) Continuation of application No. 17/123,561, filed on Dec. 16, 2020, now Pat. No. Re. 49,515, which is an application for the reissue of Pat. No. 10,512,724.

(30) Foreign Application Priority Data

Nov. 20, 2014 (SE) ..... 1451399-8

(51) Int. Cl.
*A61M 5/20* (2006.01)
*A61M 5/142* (2006.01)
(Continued)

(52) U.S. Cl.
CPC ..... *A61M 5/20* (2013.01); *A61M 5/14216* (2013.01); *A61M 5/14566* (2013.01);
(Continued)

(58) Field of Classification Search
CPC ..... A61M 5/14216; A61M 5/14566; A61M 5/32; A61M 5/20; A61M 5/178; A61M 5/5086; A61M 5/14; H04W 68/02
See application file for complete search history.

(56) References Cited

U.S. PATENT DOCUMENTS 8,361,026 B2 1/2013 Edwards et al. ..... A61P 3/10 604/137
2007/0167920 A1 7/2007 Hommann ..... A61M 5/31583 604/206
(Continued)

FOREIGN PATENT DOCUMENTS

JP 2012-507314 A 3/2012
TW 201200190 A 1/2012
(Continued)

OTHER PUBLICATIONS

International Search Report and Written Opinion for Int. App. No. PCT/EP2015/074463, completed Feb. 3, 2016.

*Primary Examiner* — Jeffrey R Jastrzab
(74) *Attorney, Agent, or Firm* — McDonnell Boehnen Hulbert & Berghoff LLP

(57) ABSTRACT

A medicament delivery device is presented having a housing that is arranged to accommodate a medicament container, a drive mechanism capable of, upon activation, act on said medicament container, a communication unit arranged in the housing, a switch operably connectable to the drive mechanism and connected to the communication unit for activating the communication unit when the switch is operated, wherein the switch is operated by the drive mechanism at the end of a dose delivery sequence.

1 Claim, 13 Drawing Sheets

(51) Int. Cl.

| | |
|---|---|
| ***A61M 5/145*** | (2006.01) |
| ***A61M 5/32*** | (2006.01) |
| ***H04W 68/02*** | (2009.01) |
| *A61M 5/14* | (2006.01) |
| *A61M 5/178* | (2006.01) |
| *A61M 5/50* | (2006.01) |

(52) U.S. Cl.
CPC ..... *A61M 5/32* (2013.01); *H04W 68/02* (2013.01); *A61M 5/14* (2013.01); *A61M 5/178* (2013.01); *A61M 5/5086* (2013.01)

(56) References Cited

U.S. PATENT DOCUMENTS

| | | | | |
|---|---|---|---|---|
| 2013/0035642 | A1* | 2/2013 | Daniel | A61M 5/2033 604/189 |
| 2013/0060196 | A1 | 3/2013 | O'Connor et al. | A61M 5/172 604/152 |
| 2013/0079708 | A1 | 3/2013 | Wimpenny et al. | A61M 5/2448 604/65 |
| 2014/0296787 | A1 | 10/2014 | Agard et al. | A61M 5/172 604/152 |

FOREIGN PATENT DOCUMENTS

| | | | | |
|---|---|---|---|---|
| WO | 2010/052275 | A2 | 5/2010 | |
| WO | 2013/098421 | A1 | 7/2013 | |
| WO | WO-2015121081 | A1 * | 8/2015 | A61M 5/2033 |

* cited by examiner

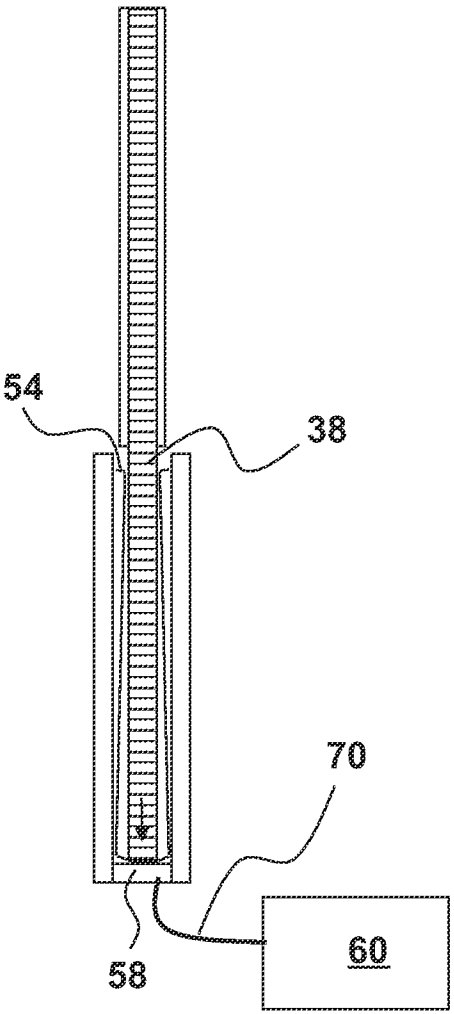
Fig. 6c
(Amended)

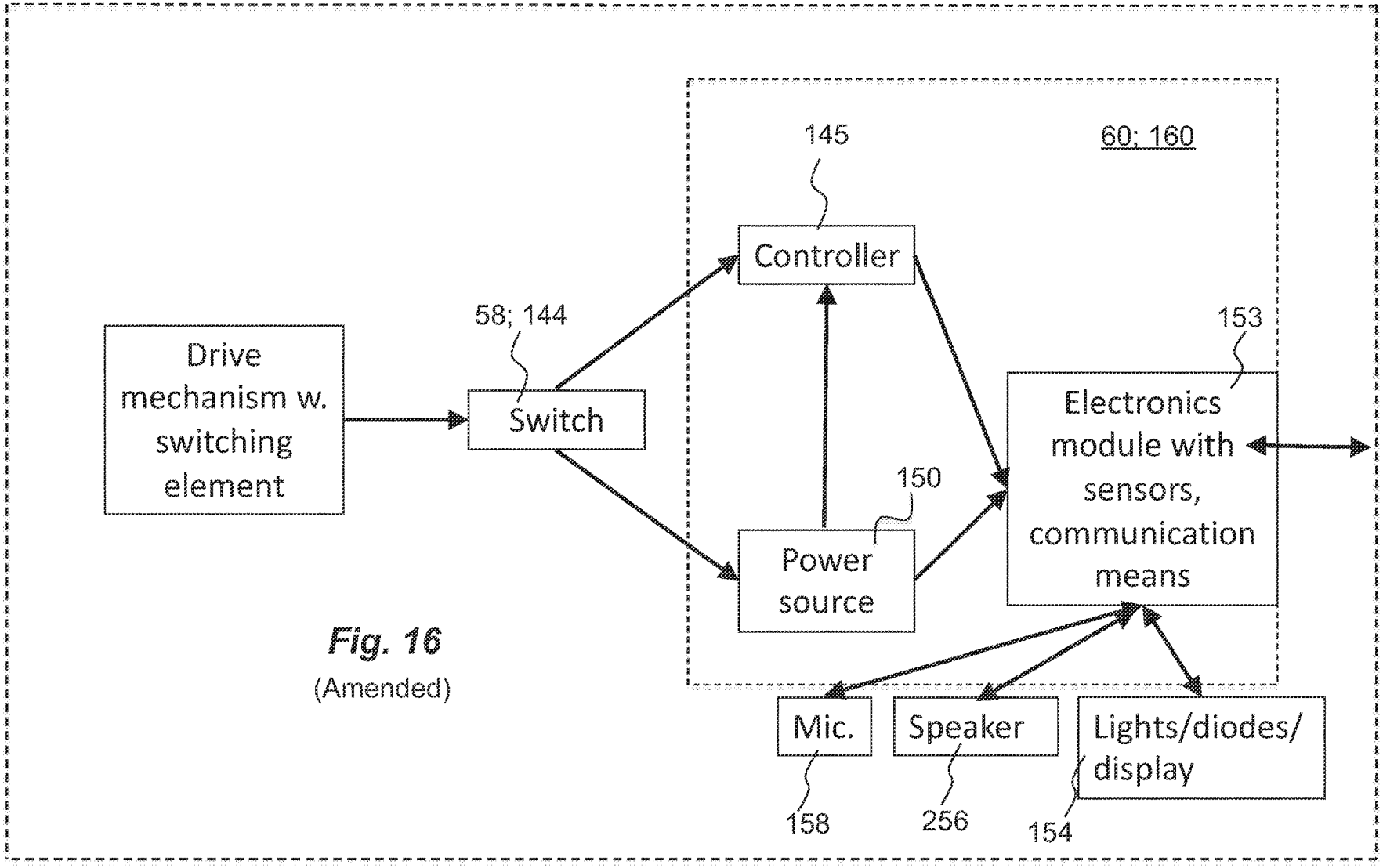
*Fig. 16*
(Amended)

MEDICAMENT DELIVERY DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a continuation reissue application of reissue application Ser. No. 17/123,561, filed Dec. 16, 2020, which is an application for reissue of U.S. Pat. No. 10,512,724, which issued on Dec. 24, 2019.*

*Notice: More than one reissue application has been filed for the reissue of U.S. Pat. No. 10,512,724. The reissue applications are the present continuation reissue application and U.S. Reissue patent application Ser. No. 17/123,561, filed Dec. 16, 2020.*

CROSS REFERENCE TO RELATED APPLICATIONS

The present application is a U.S. National Phase Application pursuant to 35 U.S.C. § 371 of International Application No. PCT/EP2015/074463 filed Oct. 22, 2015, which claims priority to Swedish Patent Application No. 1451399-8 filed Nov. 20, 2014. The entire disclosure contents of these applications are herewith incorporated by reference into the present application.

TECHNICAL AREA

The present disclosure relates to a medicament delivery device that is provided with communication capabilities.

BACKGROUND

There is a constant development of medicament delivery devices that are intended and designed to be used and handled by users that are not qualified nursing staff or physicians, i.e. handled by the patients themselves. Because the patients themselves handle the treatment, based on a specific treatment scheme, the physicians treating the patient have no direct information that the treatment schemes are followed as prescribed.

In order to obtain more information regarding the treatment, a number of devices have been developed that are capable of monitoring the dose delivery operations and to store this information. Some devices are also capable of transmitting the information to external storage locations that are accessible to a trained healthcare staff. This enables access to relevant dose delivery information to e.g. a physician of a patient.

Document U.S. Pat. No. 8,361,026 discloses a medicament delivery device that is arranged with a number of intelligent functions that may monitor the operation of the device. Among the functions are monitoring of appliance and/or adherence of the patient and uploading of the information to a suitable storage means of a remote device, where the latter could be a remote communication network, a computer, a smart phone, personal digital assistant, etc. Information could also be downloaded to the medicament delivery device to be accessible to the user, such as if the drug of a medicament in the device has been recalled by the manufacturer of the drug, that the drug has expired or updated user information. In this regard, the device is arranged with a number of switches that are activated during different functional stages.

In order for the device to function it is energized before use by pressing a start button, thus requiring a specific handling step in order to be able to use the device. Further, when the device is energized, its different electronics components and many functions will consume energy. This may be a pronounced drawback if the device is energized but not used directly for some reason. There is further a risk that the start button is operated unintentionally, thereby energizing the device by accident. If the device then is to be used at a later state, the power source of the device may be depleted of power.

BRIEF DESCRIPTION

The aim of the present disclosure is to remedy the drawbacks of the state of the art medicament delivery devices. This aim is obtained by a medicament delivery device comprising the features of the independent patent claim. Preferable embodiments of the disclosure form the subject of the dependent patent claims.

According to one aspect of the disclosure the medicament delivery device may comprise a housing, which housing is arranged to accommodate a medicament container. Further a drive mechanism is arranged, capable of, upon activation, acting on the medicament container for expelling a dose of medicament.

According to a preferable feature, a communication unit may be associated with the housing. This means that the communication unit may be integrated in the medicament delivery device or arranged as a separate unit connectable to the medicament delivery device. The communication unit may have a number of features and functions that enable communication between the medicament delivery device and the surroundings; from direct communication with the user to wireless communication with remotely located receivers and transmitters of information, such as e.g. via the internet.

The medicament delivery device preferably comprises a switch, which is operably connected to the drive mechanism and connected to the communication unit for activating the communication unit when operated. In this respect it is an advantage that the switch is operated by the drive mechanism at the end of a dose delivery sequence. This feature provides the advantage that the medicament delivery device does not have to be activated beforehand by a specific activation operation. This reduces the number of handling steps required by the user in that the switch is operated at the end of dose delivery. Further, the energy consumption is reduced in that the medicament delivery device is non-activated or "dead" until a dose of medicament has been delivered.

According to a preferred solution, the drive mechanism may further comprise a force element, which force element enables said drive mechanism to operate said switch. The force element enables an automatic operation of the drive mechanism such that the user does not have to perform the dose delivery manually. In that respect, the force element may be a drive spring arranged to act on and move a plunger rod of the drive mechanism in a proximal direction. In order to utilize the built-in force of the drive spring, it may preferably be arranged to act in a distal direction at the end of the dose delivery sequence. Thereby the residual force of the drive spring is used for activating the switch so that the communication unit is activated. Thus, no additional force elements are needed for operating the switch.

According to one feasible solution, the spring may be arranged to act on a switching element, where the switching element is arranged to be released at the end of the dose delivery sequence and to act on the switch. This solution entails a holding or locking of the switching element until the dose of medicament has been delivered. In this respect, the distal end of the drive spring may be in contact with, and act on the switching element, and when the dose has been delivered, the switching element is released and is forced in the distal direction by the drive spring, wherein the switching element is moved in contact with the switch.

As a variant, a plunger rod driver is used, wherein the drive spring is arranged to act on the plunger rod driver of the drive mechanism, such that the plunger rod driver is moved in a proximal direction acting on the switching element at the end of the dose delivery sequence. Here the contact between the plunger rod driver and the switching element causes the switch to close.

The communication unit may be arranged to communicate in a number of different ways. According to one simple and robust solution, the communication unit is arranged to communicate directly with a user. Thus, at the end of the dose delivery operation, the device may provide the user with specific information that is stored in the communication unit. The information may be audibly and/or visually presented to the user.

As an alternative, the communication unit may be arranged to communicate via a smart device. With this solution, the functionality of the smart device is used for informing the user. Thus, the end of dose operation may trigger the smart device to provide information audibly and/or visually to the user. With this solution the medicament delivery device may require fewer components and functions than if the device was to communicate directly. Regarding communication with external receivers, the medicament delivery device may be arranged with communication elements that are capable of communicating with wireless networks, comprising transmitting and receiving data. If designed such, then the medicament delivery device may transmit information regarding functions and events to for example a physician or a medical centre so monitoring the user's medicament handling and e.g. compare it with prescribed treatment schemes.

In that respect, and in order to increase the information obtainable, the communication unit may be operably connected to a number of sensors of the medicament delivery device. For example, the sensors may comprise functions that can derive information from the medicament container. The information may then be stored in many ways, such as EAN-codes, QR-codes or RFID-chips. The information from the medicament container may then be compared with information stored in databases, such as date of manufacture, batch number, date of expiry, etc. The comparison could then be used to alert the user that the date of expiry has passed and that the medicament container should be replaced with a new, that the batch has been re-called, whereby the medicament container should be discarded or sent back to the manufacturer, just to mention a few functions.

Other types of sensors may be set dose size sensors that are capable of sensing the dose that the user has set if the device is provided with such functions. Again, the set, and used, dose sizes may then be transmitted and compared with required dose sizes according to the treatment scheme. The collection of data from the medicament delivery device by the communication unit may thus be used to monitor patient adherence. In that respect, the communication unit may be arranged to obtain information regarding patient adherence, which may be communicated to the user.

In order to effectively handle the information obtained from the sensors of the device as well as the information obtained from outside and transmitted to the communication unit, it may preferably comprise data storage means. With this solution, data obtained when the medicament delivery device is used can be stored and does not have to be transmitted directly. That may be an advantage if for instance the medicament delivery device is used in a location where no communication connection can be established. The data is then firstly stored and then later transmitted to external receivers when a communication connection can be established.

According to a specific solution of the medicament delivery device, the communication unit may comprise a function for automatic connection with an emergency call centre. This may be advantageous if the medicament delivery device is designed as an emergency device that only is to be used when there is a crisis for a user, such as an allergic attack where there is a risk for anaphylaxis. The medicament delivery device may then alert an emergency call centre, wherein a connection is obtained automatically. In that respect, the communication unit may comprise a loudspeaker and a microphone for enabling speech information between user and emergency call centre.

Further, the communication unit may also comprise a positioning function, capable of obtaining the geographical position when the switch is activated, and being capable of transmitting said geographical position to the emergency call centre. This enables the emergency call centre to send appropriate paramedic help to the location of the user in need.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

FIG. 6c shows a schematic representation of the operation of several components of the drive mechanism of FIG. 3 *relative to one embodiment of the communication unit and operatively associated switch*;

FIG. 7b shows a second perspective cross-sectional view of several components of the drive mechanism *and associated switch components* of FIG. 7a;

FIG. 8b shows a second perspective cross-sectional view of several components of the drive mechanism *and switch components* of FIG. 8a;

FIG. 9b shows a second perspective cross-sectional view of several components of the drive mechanism *and associated switch components* of FIG. 9a;

FIG. 10b shows a second perspective cross-sectional view of several components of the drive mechanism *and associated switch components* of FIG. 9a;

FIG. 16 shows a communication unit according to the disclosure.

DETAILED DESCRIPTION

In the present application, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with NFC tags as well as programs capable of establishing and handling the communication with the NFC tags.

Further, in the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, etc. The medicament delivery devices may be of either disposable type or re-usable type and may be provided with medicament containers suitably arranged for specific drugs in specific forms.

Figure 1:
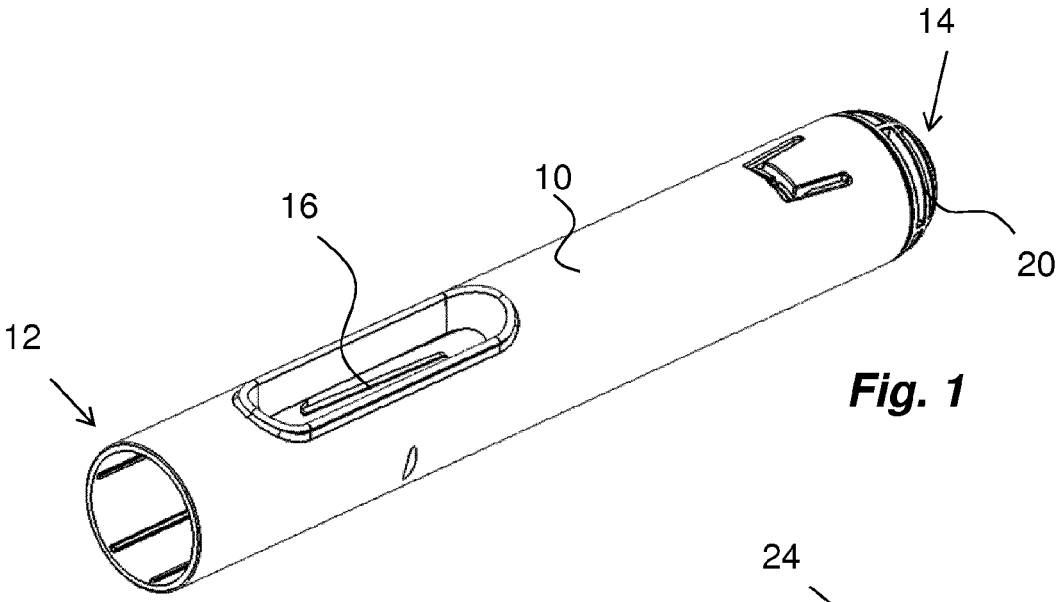
FIG. 1 shows a perspective view of the outer housing of one embodiment of the medicament delivery device of this disclosure.

As seen in FIG. 1, a medicament delivery device comprising the present disclosure may comprise a tubular housing 10 having a proximal end 12 and an opposite distal end 14. The housing 10 may further comprise a container holder 16 which is coaxially arranged within the housing for holding a medicament container 18, FIG. 3. The medicament delivery device further comprises an end cap 20 fixedly attached to the distal end 14 of the housing.

Figure 2:
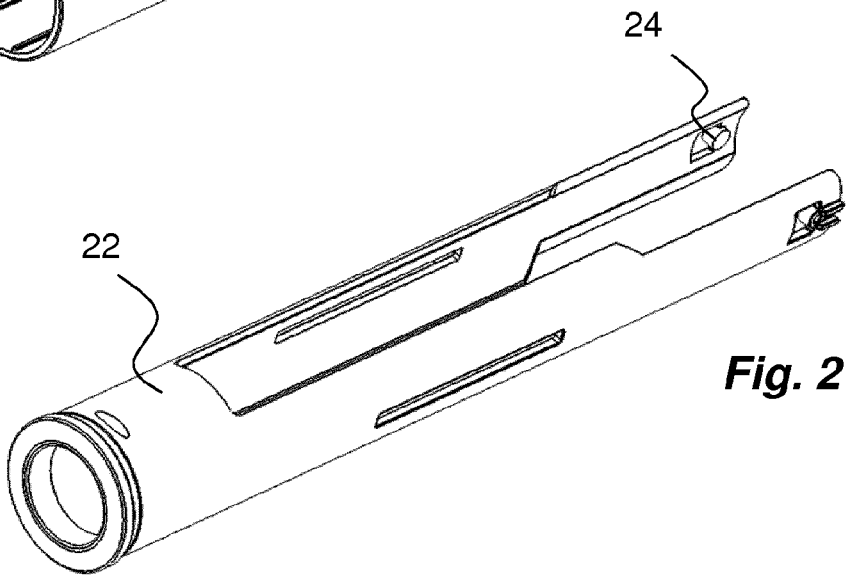
FIG. 2 shows a perspective view of the needle shield of the device of FIG. 1.

As seen in FIG. 2, the medicament delivery device may further be arranged with a tubular activation member 22 in the form of a medicament delivery member guard. The activation member 22 may be arranged with first co-acting elements 24, which in an exemplary embodiment are two protrusions, which are used for activating the medicament delivery device as will be described in detail below. According to an embodiment of the disclosure, a tension spring 25 is arranged at the proximal end of the activation member 22 for moving it in a proximal direction.

Figure 3:
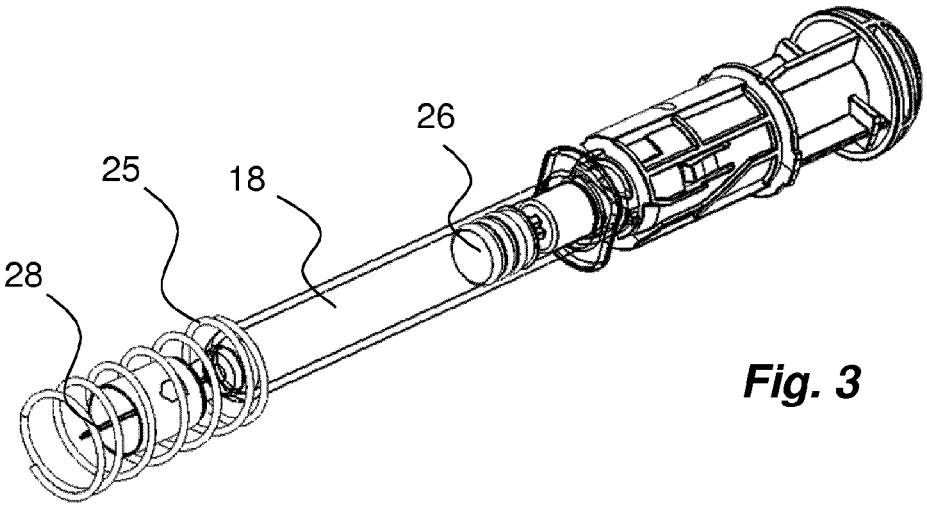
FIG. 3 shows a perspective view of medicament container and drive mechanism of the device of FIG. 1.

FIG. 3 illustrates the interior of the medicament delivery device. The medicament container 18 is arranged within the container holder 16 and has a predetermined volume of medicament, a slidable stopper 26 and a medicament delivery member 28. The medicament container 18 may be a syringe provided with a needle 28 as the delivery member; however the disclosure should not be limited to this. The medicament delivery device may also comprise a tubular rotator 30, FIG. 4a, comprising grooves 32 on its outer surface interactively connected to the protrusions 24 of the medicament delivery member guard 22, FIG. 2.

Figure 4A:
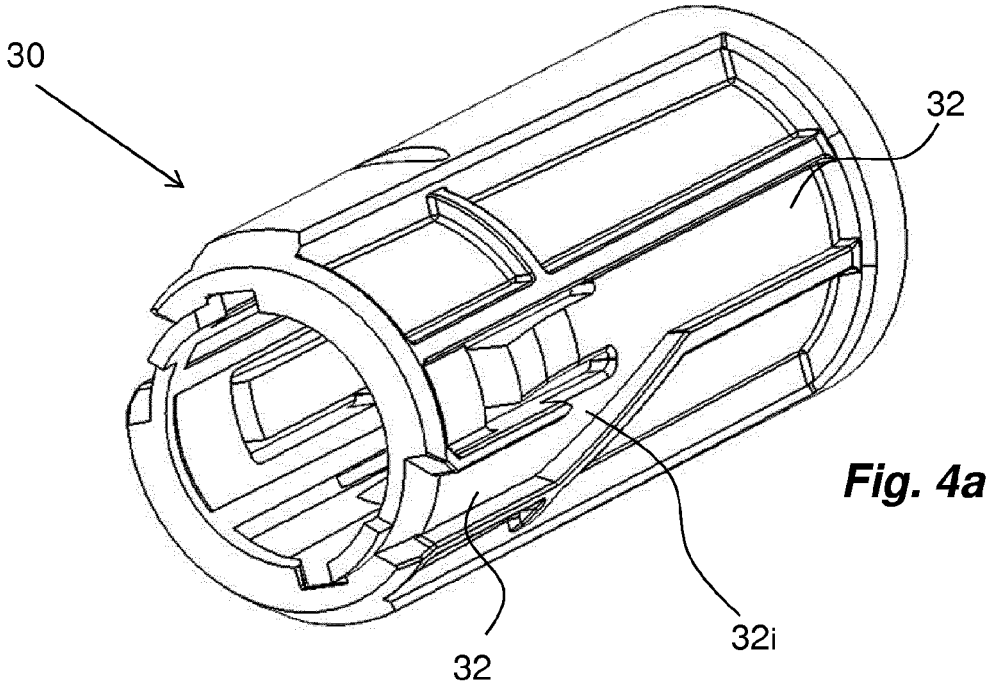
FIG. 4a shows a perspective view of a component of the drive mechanism of FIG. 3.
Figure 4B:
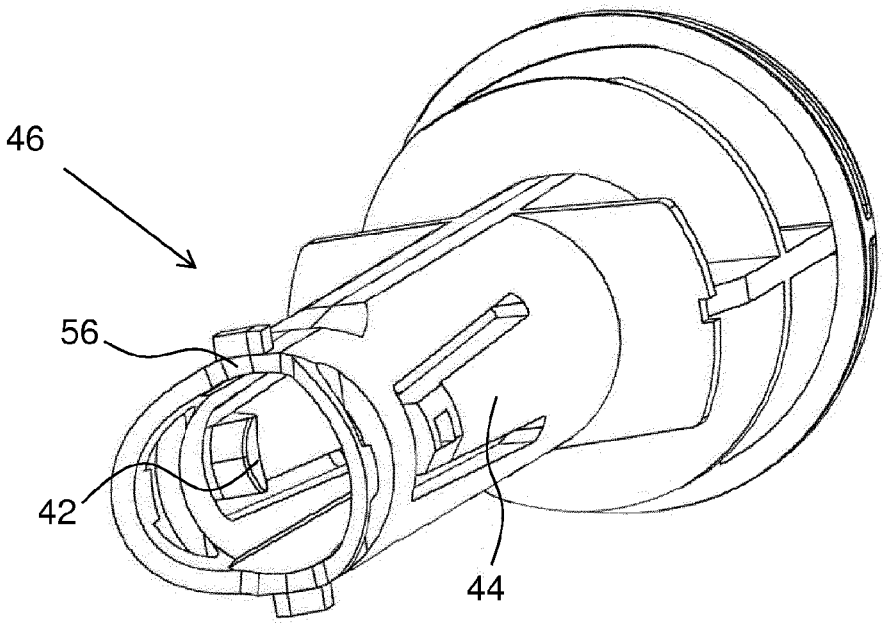
FIG. 4b shows a perspective view of a component of the drive mechanism of FIG. 3.
Figure 5A:
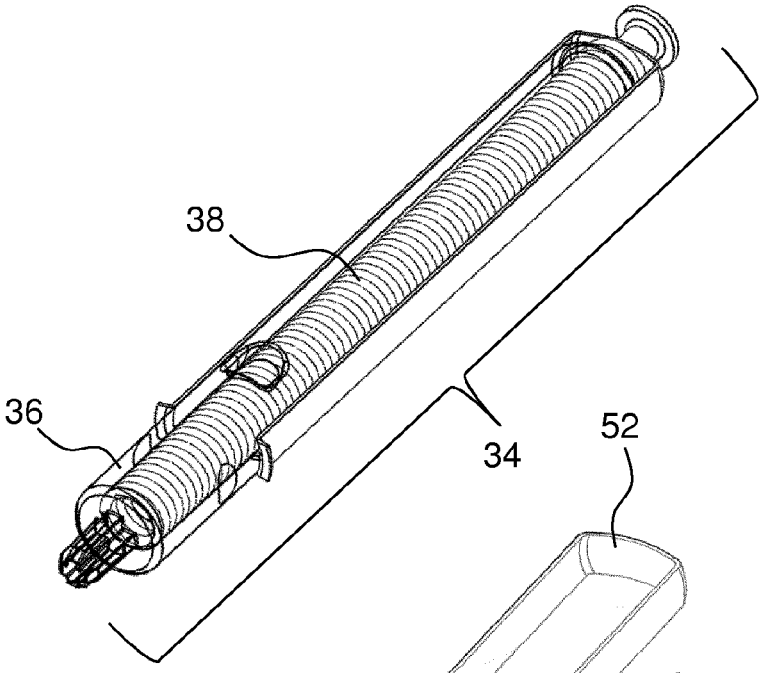
FIG. 5a shows perspective views of several components of the drive mechanism of FIG. 3.
Figure 5B:
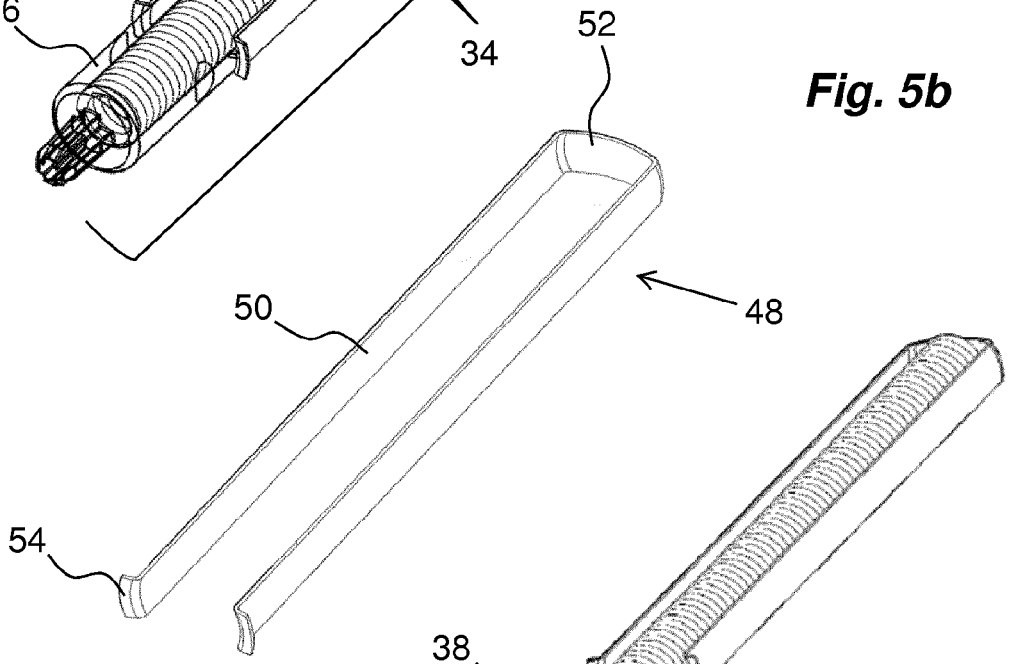
FIG. 5b shows a perspective view of a component of the drive mechanism of FIG. 3.
Figure 5C:
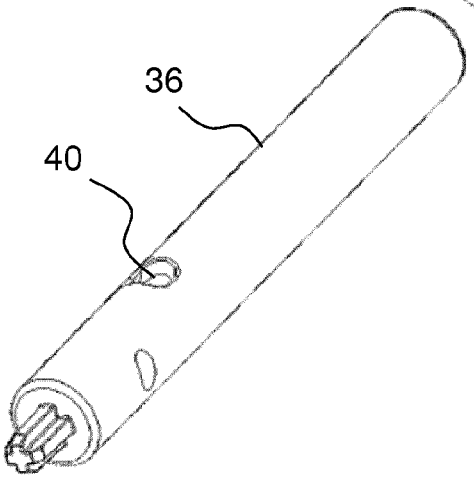
FIG. 5c shows perspective views of several components of the drive mechanism of FIG. 3.

Further the medicament delivery device comprises a drive mechanism 34, FIG. 5. The drive mechanism comprises a plunger rod 36 and a compression spring 38 arranged within the plunger rod 36. The plunger rod 36 comprises a cut-out/recess 40, FIG. 5, interactively connected to inwardly directed protrusions 42 on proximally directed flexible arms 44 of an actuator 46, FIG. 4b. The proximal end of the plunger rod 36 is in contact with the slidable stopper 26. The rotator 30, FIG. 4a, is rotatably and coaxially arranged around the actuator 46, acting on the flexible arms 44.

The drive mechanism 34 further comprises a switching element 48, the purpose of which will be described below. In the illustrated embodiment, the switching element 48 comprises an elongated u-shaped bracket, provided with at least two elongated arms 50, directed in the proximal direction, and a lower part 52, a distal transversal end wall, directed in the distal direction of the medicament delivery device. The switching element 48 may be made from metal, plastic, or any combination of these materials.

The proximal ends of the arms 50 of the switching element 48 are provided with angled support protrusions 54 extending in generally radially outward directions with regard to a longitudinal axis of the switching element 48. The arms 50 of the switching element 48 are arranged to extend along the length of the plunger rod 36, FIG. 5a, and the support protrusions 54 are adapted to rest on a proximally directed end surface 56 of the actuator 46 when the plunger rod 36 and the compression spring 38 are in a tensioned state, i.e. the inwardly directed protrusions 42 of the flexible tongues 44 of the actuator 46 are positioned in the recesses 40 of the plunger rod 36. When the plunger rod 36 and the compression spring 38 are in the pre-tensioned state, the distal end of the switching element 48 is arranged at a predetermined distance "D", FIG. 6a, from an inner distal surface of a switch 58, the function of which will be described in detail below.

The device is intended to function as follows. The user presses the proximal end of the device with the medicament delivery member guard 22 against a dose delivery site and when an injection needle is used as medicament delivery member 28, a penetration is performed on the user's skin. The penetration causes the housing 10 to be moved in the proximal direction in relation to the medicament delivery member guard 22. This in turn causes the protrusions 24 of the medicament delivery member guard 22 to move in the grooves 32 of the rotator 30 such that the protrusions 24 will come in contact with inclined groove sections $\mathbf{32}_i$, which will cause the rotator 30 to turn around the longitudinal axis of the medicament delivery device.

The turning of the rotator 30 will activate the drive mechanism 34 in that the arms 44 of the actuator 46 are freed. The arms 44 may then flex outwardly, whereby the inwardly directed protrusions 42 of the arms 44 are moved out of contact with the recesses 40 of the plunger rod 36. The drive spring 38 of the plunger rod 36 now urges the plunger rod 36 in the proximal direction for expelling a dose of medicament through the medicament delivery member 28 until the stopper 26 of the medicament container 18 reaches its most proximal position.

Figure 6B:
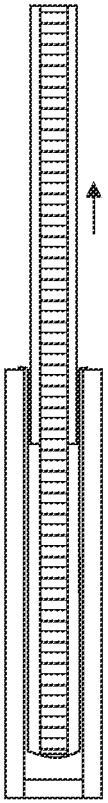
FIG. 6b shows a schematic representation of the operation of several components of the drive mechanism of FIG. 3 *relative to one embodiment of the communication unit and operatively associated switch*.
Figure 6A:
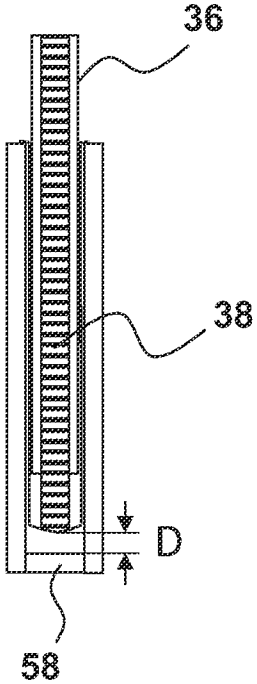
FIG. 6a shows a schematic representation of the operation of several components of the drive mechanism of FIG. 3 *relative to one embodiment of the communication unit and operatively associated switch*.

When the stopper 26 has been moved by the plunger rod 36 to almost the proximal end inside the medicament container 18, the plunger rod 36 is moved out of contact with the arms 50 of the switching element 48 as seen in FIG. 6c. The arms 50 of the switching element 48 are thus free to flex inwards such that the support protrusions 54 are moved out of contact with the surfaces 56 of the actuator 46, and due to the force of the compression spring 38 in contact with and acting on the lower part 52 of the switching element 48, the switching element 48 will be moved suddenly in the distal direction the distance D until the distal end of the switching element 48 hits the switch 58, thereby activating the switch 58, FIG. 6c. The activation of the switch will in turn activate a communication unit 60, i.e. powering the communication unit. The function of the communication unit will be described in detail below.

Figure 7B:
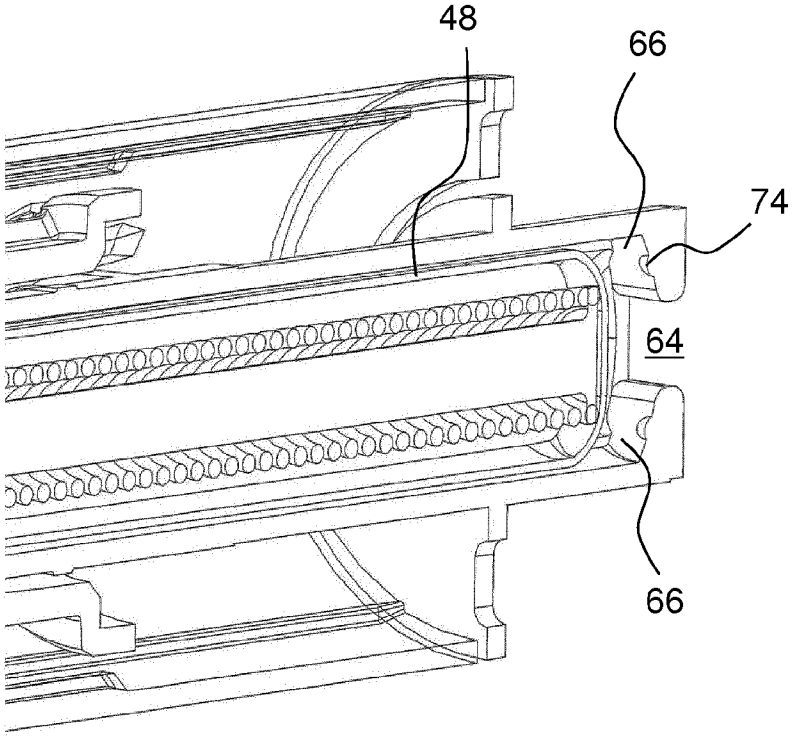
Figure 7A:
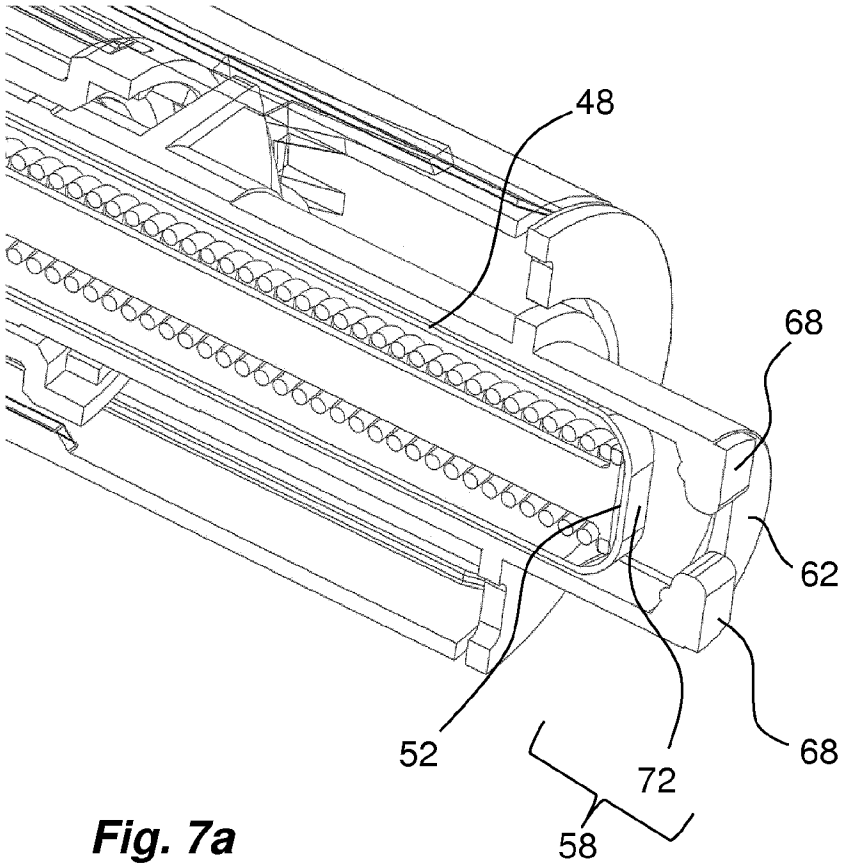
FIG. 7a shows perspective cross-sectional view of several components of another embodiment of a drive mechanism *and associated switch components* of the present disclosure.
Figure 8B:
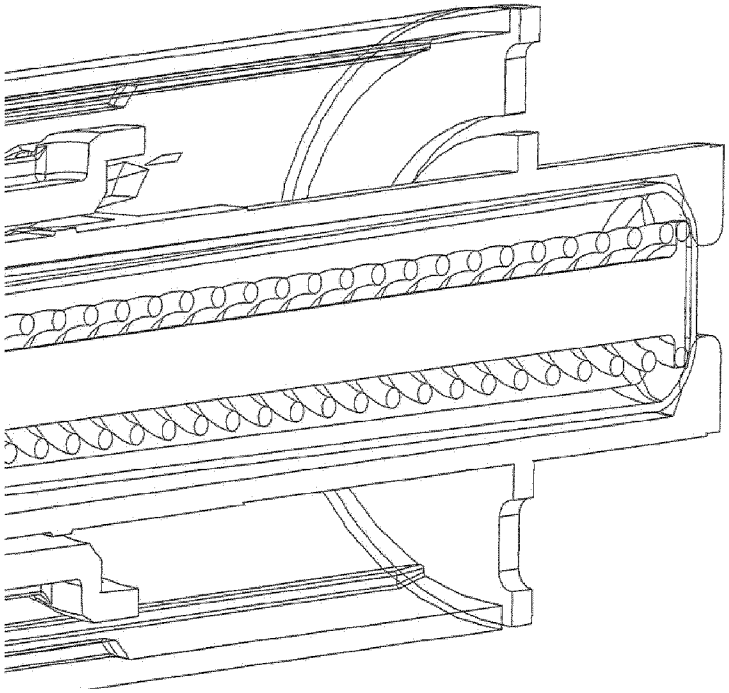
Figure 8A:
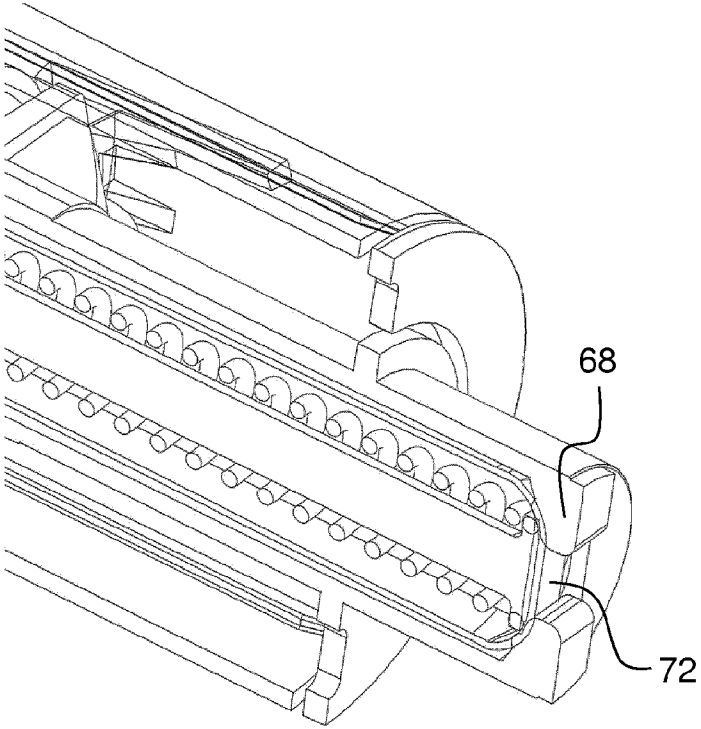
FIG. 8a shows a perspective cross-sectional view of several components of the drive mechanism *and associated switch components* of FIG. 7a in a different operational state.

It is to be understood that the switch may have a number of different designs depending on the type of device and its operating components as well as the kind of signal that is to be obtained. FIGS. 7 and 8 show one type of switch that can be used with the switching element described in connection with the above embodiment.

Here a distal end of the actuator 46 is arranged with an end wall 62, provided with a generally rectangular cut-out 64. On opposite sides of the cut-out, two proximally directed, somewhat inclined, contact surfaces 66 are arranged, which surfaces the switching element 48 will hit when released. The inclined contact surfaces are provided with conductive material. The conductive material extends through the cut-out 64 as leads 68, wherein suitable conduits 70, FIG. 6c, are connected to these leads 68 and then extend to the communication unit 60. Further, the switching element 48 may be made of metal, such that when the switching element 48 is moved in contact with the contact surfaces 66, the switch is closed. As an alternative the distal end surface 72 of the switching element may also be covered with conductive material. The contact surfaces 66 may further be arranged with protrusions 74, FIG. 7b, in order to enhance the contact reliability between the switching element 48 and the contact surfaces 66. FIG. 8 show when the switching element is moved in contact with the contact surfaces.

Figure 9B:
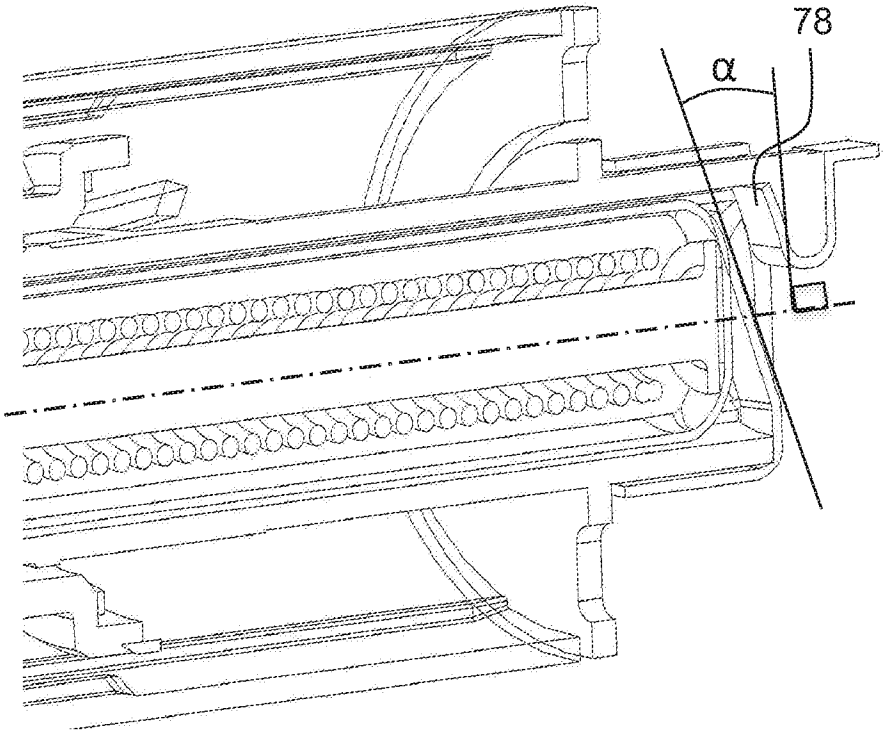
Figure 9A:
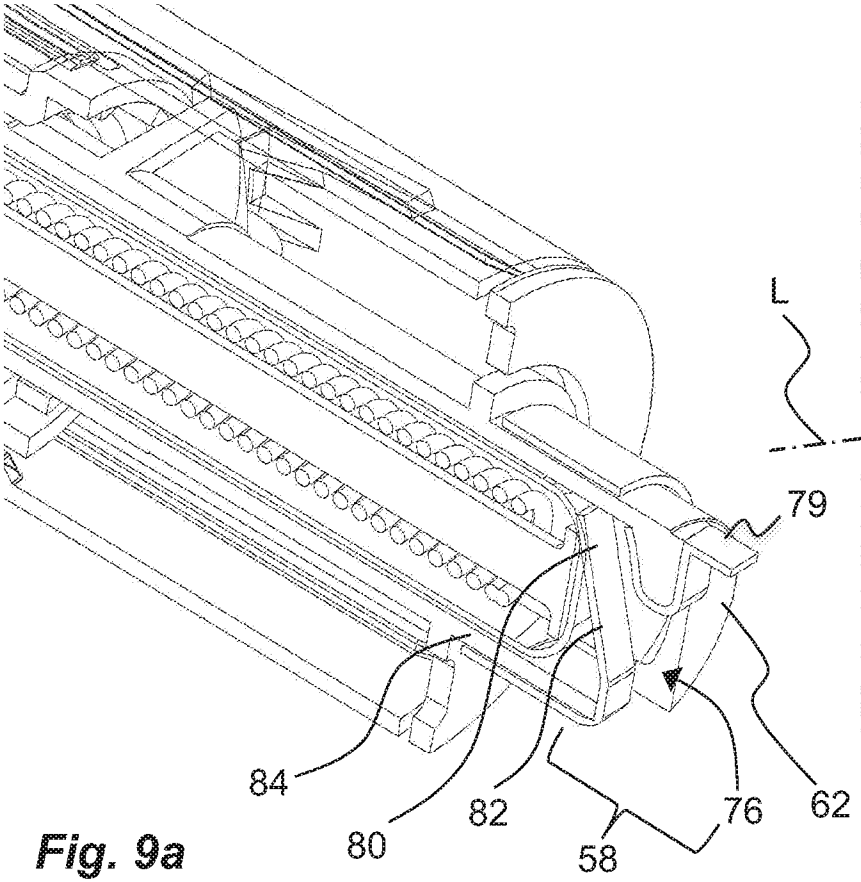
FIG. 9a shows perspective cross-sectional view of several components of another embodiment of a drive mechanism *and associated switch components* of the present disclosure.
Figure 10B:
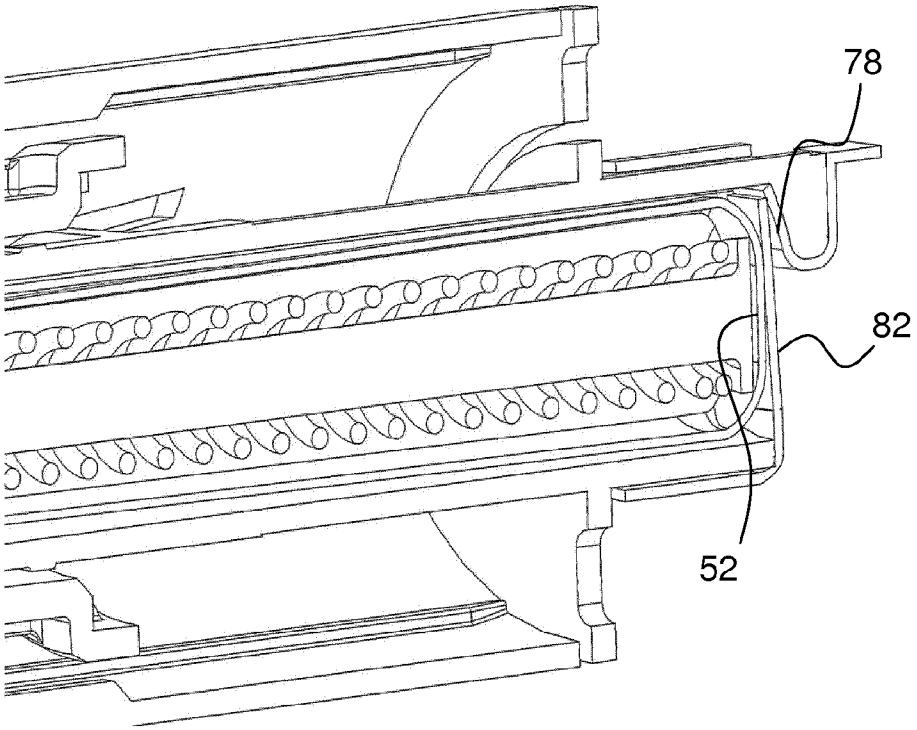
Figure 10A:
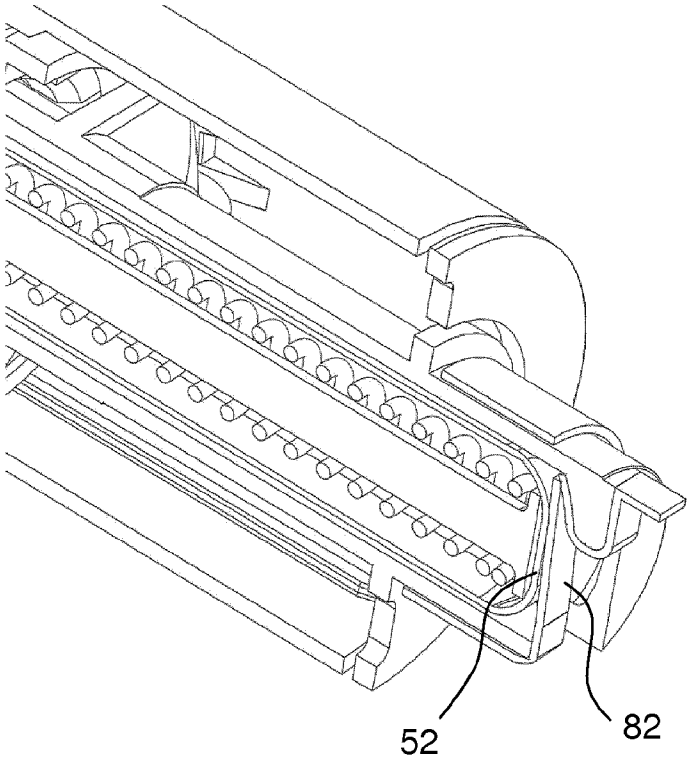
FIG. 10a shows a perspective cross-sectional view of several components of the drive mechanism *and associated switch components* of FIG. 9a in a different operational state.

FIGS. 9 and 10 display another embodiment of a switch to be used with the medicament delivery device described above. Also here, the actuator is arranged with an end wall 62 at its distal end. The end wall 62 is arranged with a generally rectangular cut-out 76. One proximally directed, somewhat inclined, contact surface 78 is arranged adjacent one edge of the cut-out. The contact surface is arranged with conductive material, which extends through the cut-out as a lead 79, wherein a suitable conduit is connected to this lead, which conduit is connected to the communication unit 60. Further, a contact element 80 is arranged. It comprises a tongue 82 of a flexible material extending into the interior of the actuator with an inclination a in relation to a normal of the longitudinal axis L of the medicament delivery device when in unaffected, initial, position. Further, in the unaffected, initial, position there is a certain gap between the free end of the tongue 82 and the contact surface 78. Even though the tongue 82 is arranged to be flexible it is understood that it should be so rigid that the tongue 82 cannot be moved in contact with the contact surface if the medicament delivery device is dropped on the floor for instance.

The tongue 82 is attached to, or made integral with, a generally tubular seat 84 surrounding a distal part of the actuator 46. The seat 84 is further arranged with conductive material and is connected to the communication unit 60 via a suitable conduit 70. When the switching element 48 pushes on the tongue 82 in the distal direction with its lower part 52, whereby the tongue 82 is moved in contact with the contact surface 78 and the switch is closed, as seen in FIG. 10. In this embodiment, the switching element may be of any suitable material; it does not have to be made of metal.

Regarding the contact surfaces and the leads of the embodiments described above, they can be created in many ways. They can be made by thin conductive sheet material that is bonded to components in suitable ways, such as gluing. As an alternative, the Laser Direct Structuring (LDS) technology may be utilized in creating conductive surfaces on different components. In this regard, the switching element of the first switch embodiment may be of a non-conductive material, where the distally directed end surface is treated with a conductive material, for instance with LDS.

FIGS. 11-15 disclose a second embodiment of a medicament delivery device comprising the present disclosure. The embodiment shown in the drawings comprises a generally elongated main housing 100 having a distal end 102 and a proximal end 104, FIG. 11.

Figure 14:
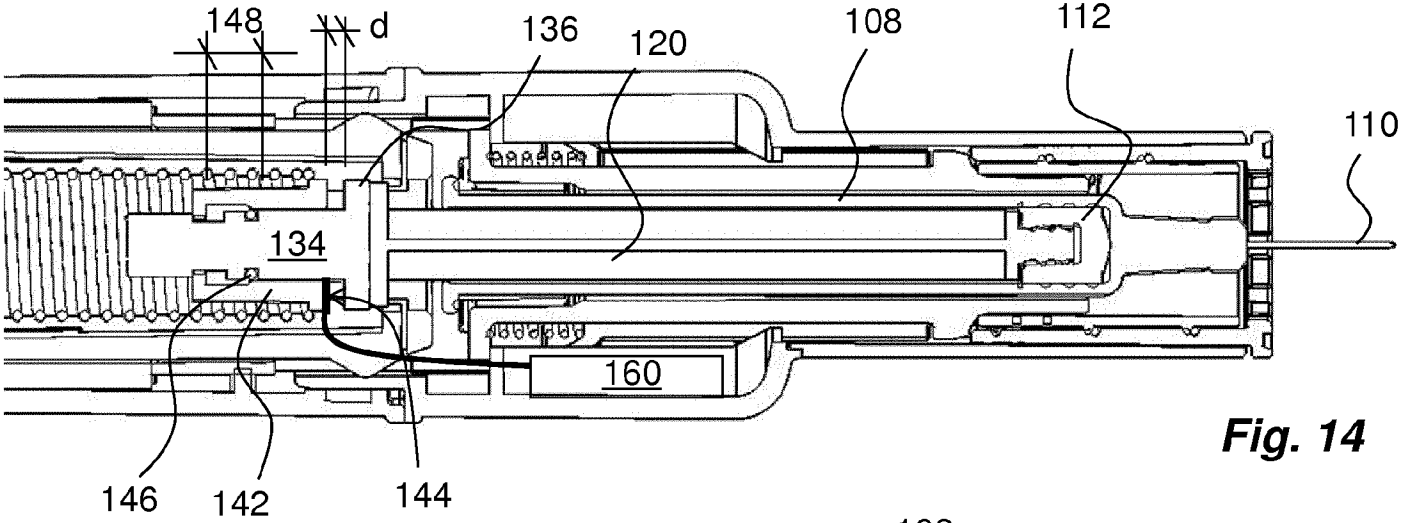
FIG. 14 shows a cross-sectional view of the drive mechanism of FIG. 12 on a first operational state.

The housing 100 is designed to accommodate a medicament container 108, FIG. 14. An appropriate medicament delivery member 110, FIG. 14, is attached to, or made integral with, the medicament container 108. A movable stopper 112 is further arranged inside the medicament container, FIG. 14.

Figure 11:
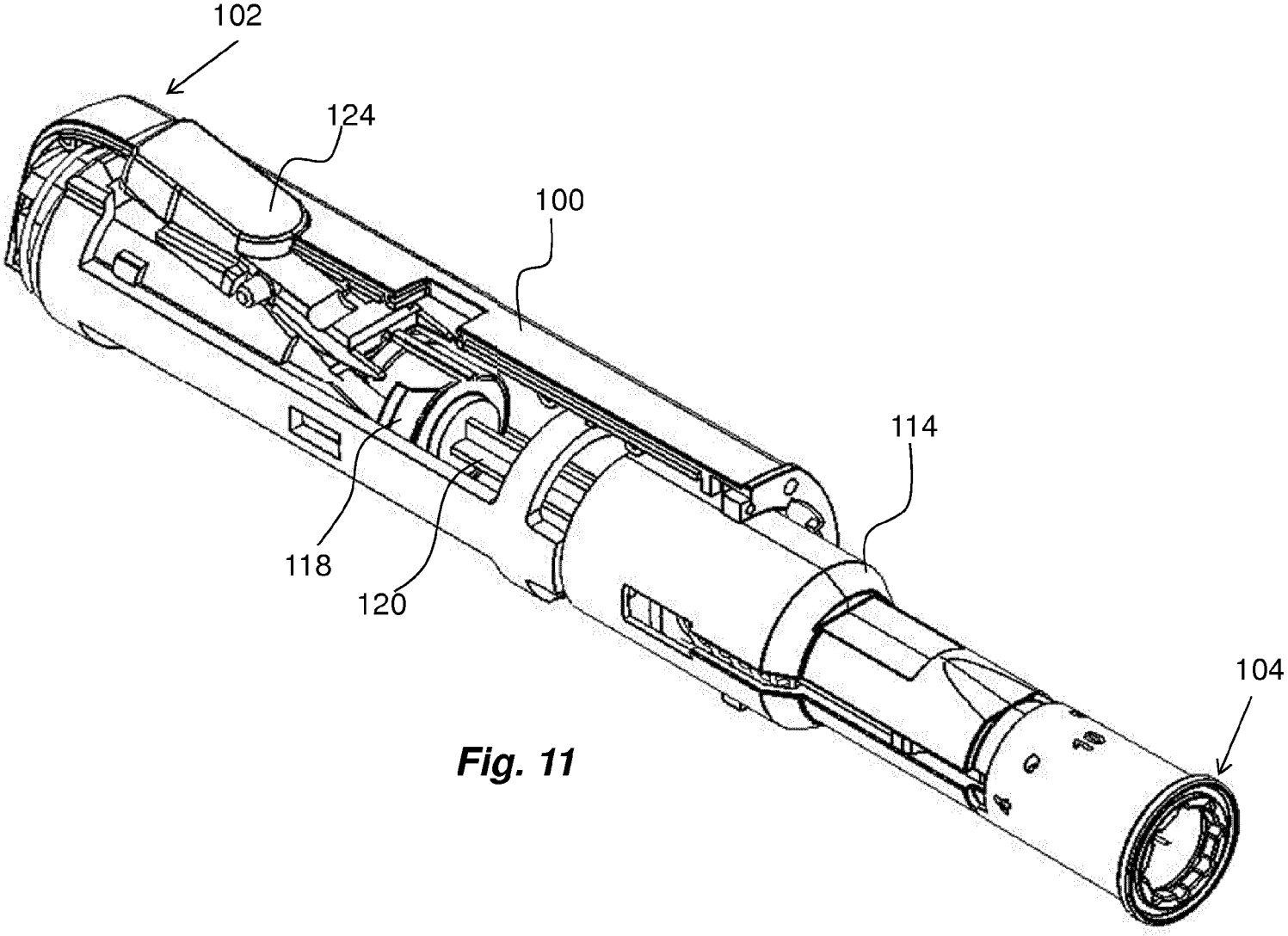
FIG. 11 shows a perspective view partly dis-assembled of a second embodiment of a medicament delivery device comprising a communication unit.

Surrounding the medicament container 108 and coaxial therewith is a medicament delivery member shield 114, FIG. 11. The medicament delivery member shield 114 can move in the longitudinal direction in relation to the housing 100.

Figure 13:
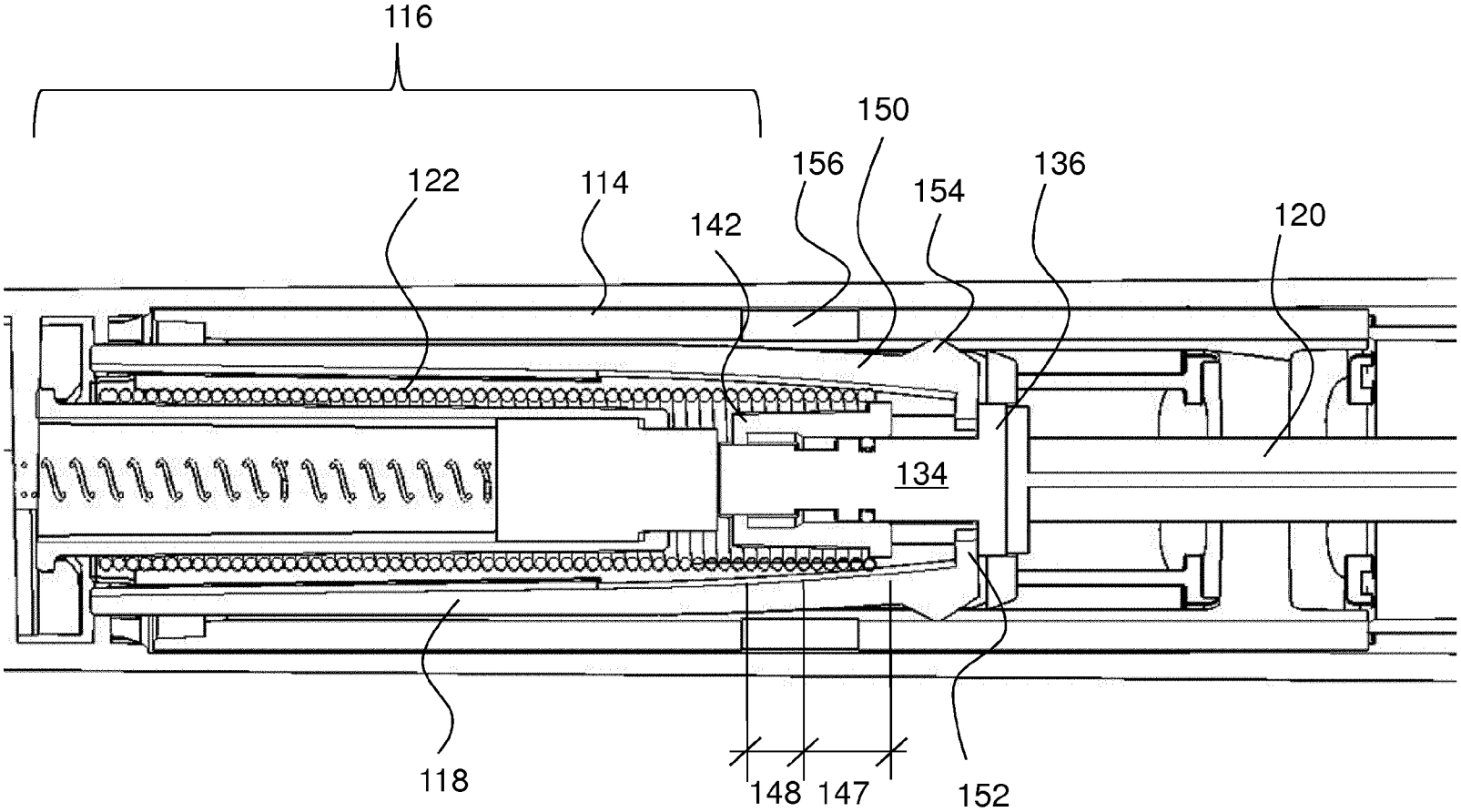
FIG. 13 shows a cross-sectional view of the drive mechanism of FIG. 12.

The device further comprises a drive mechanism 116, FIG. 13. The drive mechanism 116 comprises a plunger rod driver 118 arranged axially moveable within the housing 100. The proximal end of the plunger rod driver 118 is operably connected to a distal end of an elongated plunger rod 120, FIG. 11.

The drive mechanism 116 further comprises a drive spring 122, here in the form of a helical coil spring, FIG. 13, which biases the plunger rod driver 118 towards its proximal end position. A manually operated release button 124, for releasing the plunger rod driver 118 of the drive mechanism 116 from the distal, or cocked, position to the proximal, or extended, position is arranged extending through the housing 100, FIG. 11. The release button 124 is operably connected to a drive mechanism locking element 126 which locks and interworks with the plunger rod driver 118 via a proximally directed ledge 128 positioned in a groove 130 to hold the plunger rod driver 118 with the drive spring 122 in the tensioned state.

According to the second embodiment, the drive mechanism 116 is arranged with a switching mechanism. It comprises a switching element 132, FIG. 12, comprising an elongated tubular body 134, provided with a circular end plate 136 with a proximally directed end surface, which is intended to be in contact with a distally directed end surface of the plunger rod 120. Further, the side surface of the body 134 of the switching element 132 is arranged with a circumferential groove 138, FIG. 12. The body 134 is arranged to fit into a central passage 140 of a tubular element 142 attached to a proximal area of the plunger rod driver 118, FIG. 13.

Figure 12:
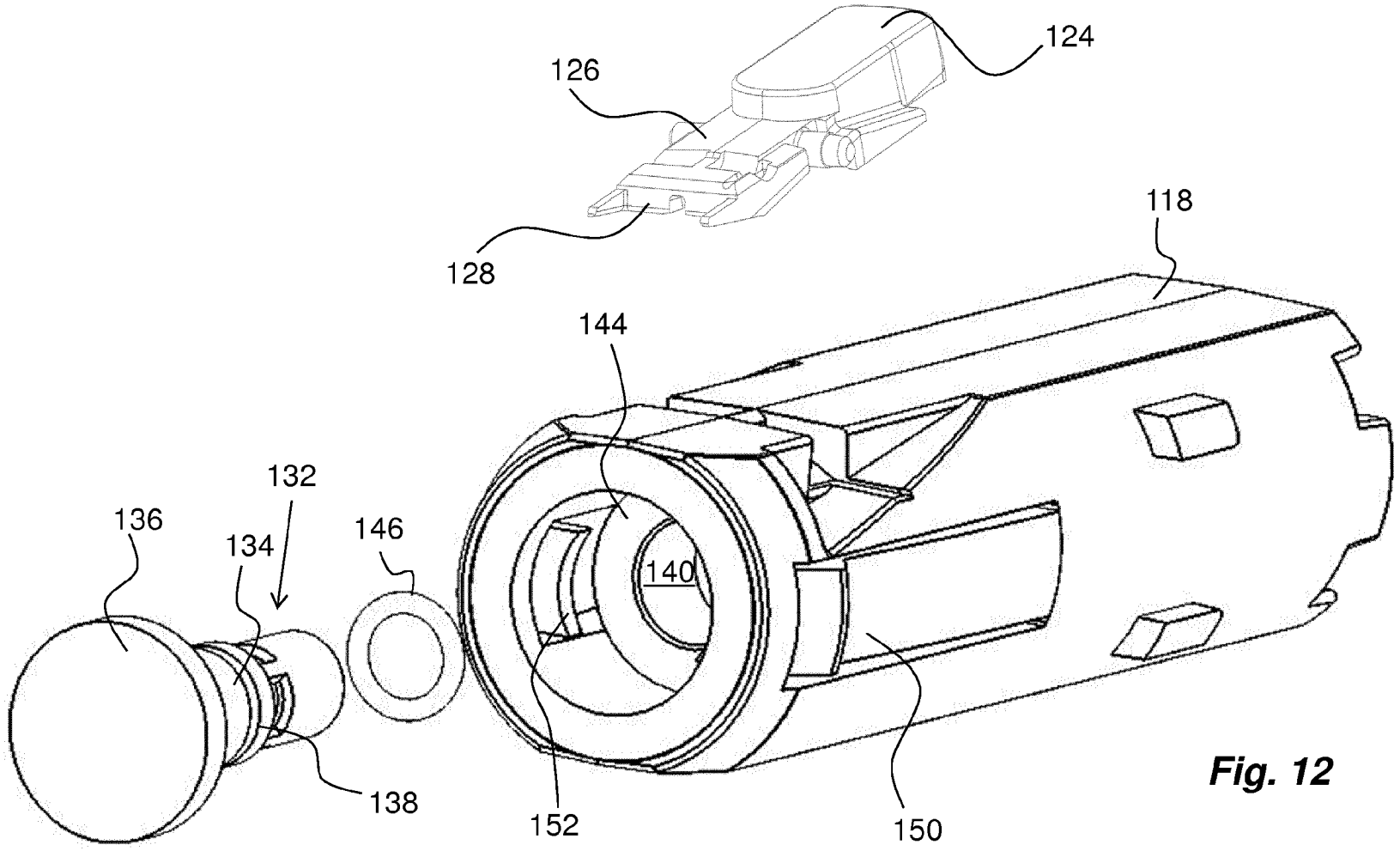
FIG. 12 shows an exploded perspective view of several components of a drive mechanism of the present disclosure.

The tubular element 142 is arranged with a proximally directed annular switch 144 at the proximal end of the plunger rod driver 118, FIG. 12. The switch 144 can be of many different configurations and designs. For example, the switch 144 may be a piezo-electric element capable of providing an electric signal when mechanically affected. Further, the switch can also be a mechanical contact having electric contact points that are brought in contact when the switch is mechanically affected as will be explained below. The switch 144 is further connected to a microcontroller 145 of a communication unit 160 of the medicament delivery device, FIG. 16, arranged to perform a number of functions as will be described.

The area of the plunger rod driver 118 proximal of the switching element 132 has a diameter somewhat larger than the diameter of the end plate 136, such that the latter may fit into the proximal end of the plunger rod driver 118, as seen in FIG. 12.

Preferably the device is arranged with a switching delay mechanism. It comprises a friction enhancing element 146 intended to fit into the circumferential groove 138 of the switching element 132. In the embodiment shown the friction enhancing element is an O-ring made of a resilient material such as rubber. The central passage 140 of the tubular element 142 is arranged with a first section 147, FIG. 13, having a diameter somewhat smaller than the diameter of the O-ring when fitted into the circumferential groove such that the O-ring is compressed when placed in the first section 147. The central passage is further arranged with a second section 148, FIG. 13, which has a diameter that is slightly larger than the diameter of the O-ring, the function of which will be described below.

Further, a switching mechanism for the release mechanism is provided on the plunger rod driver 118. It comprises two arms 150, FIG. 13, attached to the plunger rod driver 118 and extending in the proximal direction, where the arms 150 are positioned on opposite sides of the central passage 140. Each arm 150 is arranged with a generally radially inwardly directed ledge 152. The inwardly directed ledges 152 are arranged to extend into the central passage 140. Further the arms 150 are arranged with generally radially outwardly extending ledges 154, the function of which will be described below.

This second embodiment is intended to function as follows. When to be used, the proximal end of the medicament delivery device is pressed against a dose delivery site. The user depresses the trigger button 124, whereby the drive spring 122 is released. The plunger rod driver 118 and the drive spring 122 then acts to force the plunger rod 120 in the proximal direction acting on the stopper 112 inside the medicament container 108. Since the medicament is incompressible and the passage through the medicament delivery member 110 is narrow, the medicament container 108 will be moved in the proximal direction. The movement of the medicament container 108 will now cause a penetration of the medicament delivery member 110 into the skin of the user.

The force of the drive spring 122 now forces the plunger rod 120 in the proximal direction in relation to the medicament container 108, moving the stopper 112 in the proximal direction, whereby a dose of medicament is delivered into the body of the user. When the plunger rod 120 is moving in the proximal direction, so is the switching element 132. This is due to the arms 150 being forced radially inwards due to the outwardly directed ledges 154 being in contact with an inner surface of the medicament delivery member guard 114 as seen in FIG. 13. The inwardly directed ledges 152 of the arms 150 are then abutting a distally directed surface of the end plate 136 of the switching element 132.

Figure 15:
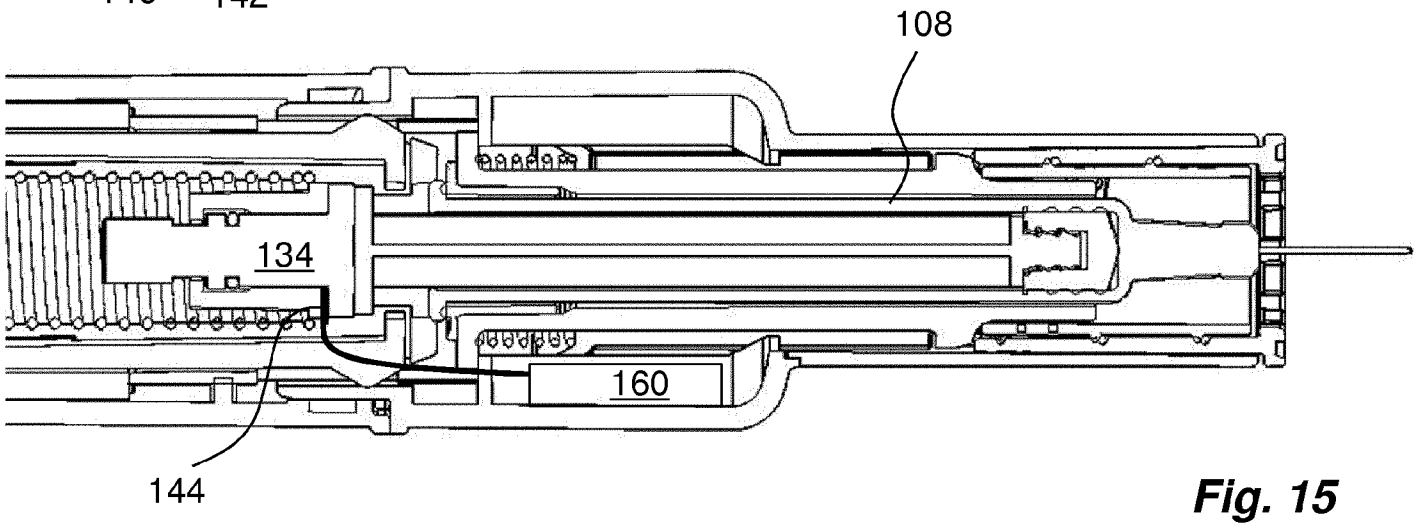
FIG. 15 shows a cross-sectional view of the drive mechanism of FIG. 14 in a second operational state.

When the plunger rod driver 118, the switching element 132, the plunger rod 120 and the stopper 112 have reached a position close to the proximal end position of the stopper 112, the outwardly directed ledges 154 of the arms 150 will enter cut-outs 156 of the medicament delivery member shield 114, FIGS. 14 and 15. The arms 150 are then free to move radially outwardly when the outwardly directed ledges 154 enter the cut-outs 156. Thereby, the inwardly directed ledges 152 will be moved out of contact with the end plate 136 of the switching element 132.

The force of the drive spring 122 will continue to urge the plunger rod driver 118 in the proximal direction in relation to the switching element 132. However, the relative movement between the plunger rod driver 118 and the switching element 132 is slowed due to the friction enhancing element 146 frictionally acting on the inner surface of the tubular element 142 of the plunger rod driver 118. The friction also aids in transferring some force to the plunger rod 120, ending the injection sequence.

The relative movement continues between the plunger rod driver 118 and the switching element 132. When the friction enhancing element 146 has been moved along the first section 147 it reaches the second section 148, as seen in FIG. 14. Now the friction enhancing element 132 is moved out of contact with the inner surface of the tubular element 142. As seen, the distally directed surface of the end plate 136, is positioned a distance d from the switch 144 as seen in FIG. 14. The force from the spring 122 still acts on the plunger rod driver 118 and since it now can move freely, it will accelerate in the proximal direction the distance d until the distally directed surface of the end plate 136 comes in contact with the switch 144, as seen in FIG. 15. The switch then activates the communication unit 160 of the medicament delivery device.

According to the disclosure, the activation of the device may cause a number of functions to be performed, all depending on the intended and desired use of the device.

According to one aspect of the disclosure the switch, when activated, will for example trigger the microcontroller 145 of the communication unit by connecting it to a suitable power source 250 arranged in the device, FIG. 16. A power source may e.g. be a battery such as a button cell or the like. Other types of power sources may be piezo elements, solar cell panels or the like. The microcontroller 145 is arranged to control at least one electronics module [152] *153* of the communication unit 60, 160 that may be arranged with different types of sensors. The electronics module may also be energized by the power source.

The electronics module may now perform a number of different functions either alone or in combination with other functions. One basic function that the electronics module may perform is to communicate directly with the user of the device. This communication may be done visually, e.g. by text stored in the electronics module that is displayed on a suitable display 154 on the device. In addition to, or instead, the communication may be performed audibly, e.g. by a recorded message stored in the electronics module that is played in an appropriate loudspeaker 256 of the electronics module or of the device as such.

In this regard, the electronics module may be arranged with a communication module that is capable of communicating with other devices, preferably wireless. Feasible communication systems are Bluetooth, ANT, mobile communication systems such as GSM, 4G, 5G, wlan etc, such that the device may communicate its status to a suitable receiver.

A suitable receiver may be databases set up for handling information from medicament delivery devices. The databases may be set up to communicate back to the user via the communication unit of the medicament delivery device, providing the user with specific information. In this respect, the information may be transmitted from the databases via the wireless networks, or may be stored beforehand in the communication unit and activated by a transmitted signal from the databases.

Regarding the information that the user may receive, either stored or received on activation, may be of different nature depending on the type of device, user prescription, type of drug, etc.

For example, if the device is a disposable injection device, the user may then be prompted to discard the device in a safe way, e.g. placing it in a safe container. In addition, the information may ask the user to attach a protective cap on the medicament delivery member in order to avoid damages. On the other hand, if the device is a reusable, the information may be to replace the used medicament container with a new container in order to make the device ready for a subsequent dose delivery. Also, the user may be prompted to remove the used medicament delivery member and to replace it with a new, sterile medicament delivery member.

The user information may further comprise an indication when the next dose should be taken, based on pre-determined prescription scheme. This scheme may be stored in the electronics module, or in the smart device or in the cloud and down-loaded to the medicament delivery device or the smart device upon activation. Other types of information may be how to store the medicament delivery device regarding temperature and/or light exposure.

The information from the electronics module may include features that are important to for example a physician of the patient/user. The information may then include event data such as time and date when the medicament was delivered to the user. In this respect, the activation of the electronics module may trigger the recording/logging of the date and time of the activation. This storage may be done in the electronics module if it has the means of obtaining such information from outside the medicament delivery device. Further, the information may be stored on the internet in that a signal from the electronics module, either direct or via a smart device, will trigger a time and date registration on a computer or in a database connected to the internet.

Event data may further include replacement of a used medicament container with a new medicament container. In that respect, when the medicament delivery device has been activated by the switch, a number of sensors can be used and activated in the medicament delivery device. For example, a sensor may be arranged that is capable of sensing the presence of a medicament container. In its simplest design, the sensor may be a proximity sensor or even a contact switch that is affected by the presence and/or removal of a medicament container.

The sensor may further be more intelligent in that it may be capable of deriving certain information. In that respect, the medicament container may be arranged with information that is specifically connected to the drug inside the medicament container. The information may comprise the type of drug, the concentration or strength of the drug, the expiry date of the drug, if there are any temperature requirements, etc. This information may be stored in appropriate ways on the medicament container, preferably such that it cannot be tampered with or compromised. The information may for example be arranged on a label that is firmly attached to the outer surface of the medicament container. The information may then be presented in different forms such as EAN-code, QR-code or the like readable code.

The medicament delivery device may in that respect be arranged with appropriate sensors or readers that are capable of deriving information from those types of code. The labels may instead be arranged with radio-frequency chips or RFID-chip, and suitably NFC-chips. The sensors are then arranged to read the chips and to derive information stored thereon. This information may then be communicated to either a smart device and/or to wireless networks. Further, the use of NFC-chips enable the reading of the chip by a smart device, if the latter is arranged with a function enabling reading of NFC-chips. Further, instead of using labels, the NFC-chips may be embedded in the material of the medicament container in order to further minimize the risk of manipulating the information.

Regarding temperature, there is a possibility of obtaining information regarding if the medicament container has been expose to temperatures outside certain approved ranges in that the NFC-chip is provided with temperature sensors. Should the medicament container have been exposed to temperatures outside the approved, this may be read from the NFC-chip.

The triggering of the medicament delivery device by the end of dose switch may provide further information. For instance, the electronics module may be arranged with a positioning function whereby the geographical position of the user may be obtained and used for different purposes. In this respect, the positioning may be obtained by different functions. Either the electronics module is provided with a GPS-function, whereby the actual position of the user when the dose is delivered is recorded by GPS coordinates. Another possibility is to use the GSM-function for locating the position. The GPS-function and the GSM-function may further be combined with a WIFI location function for improved indoors location.

The accuracy of the positioning function is dependent on the purpose of the location information. For instance if it is important to know if the drug is used in the right country, for instance to be able to track that the drug is not imported or sold to others if the user has received the drug for free or with large subsidies, then it is only necessary to obtain country-based positioning information. In that case the GSM-function may be used to obtain information in which country the medicament delivery device is used.

On the other hand, if the medicament delivery device is a so called emergency device, which is to be used only when an emergency occurs like for instance if a patient suffers an allergic attack that results in an anaphylaxis, then the positioning accuracy may be important. The anaphylaxis may be treated by epinephrine and several patients have been provided with auto-injectors filled with epinephrine. However, if such a medicament delivery device was used, there is still a risk that the patient needs further care if for instance the injection of epinephrine was not completely successful. In that case it might be very important that the positioning of the patient is precise and accurate so that paramedics can find the patient. Therefore a GPS-function should preferably be used, maybe also together with a WIFI or network positioning function in order to derive positioning information from both. The GPS-function should preferably be transmitting continuously until the medicament delivery device is switched off or the battery is depleted. This is because the emergency use of the medicament delivery device may take place on a moving vehicle, whereby the position of the patient is changing. In order for the paramedics to then find the patient, they need to receive the position continuously.

The signalling from the emergency device may further result in an automatic emergency call to a health care call centre. The patient may then talk directly to a physician or a nurse via a microphone 158, wherein they can acquire the state of the patient. The call may be performed by the medicament delivery device, if provided with such functionality and with loudspeaker and microphone.

The positioning functionality may either be arranged in the medicament delivery device directly or may be incorporated in a smart device that can communicate with the medicament delivery device. However, when the positioning functionality is used for an emergency device, then it might be more advantageous that the positioning function is comprised directly in the device, because otherwise the signalling is dependent on two devices. This is a disadvantage because the patient might not have the smart device with him, or the smart device is dead due to depleted batteries.

As an alternative, the medicament delivery device may in addition be used together with a smart device. The communication unit of the medicament delivery device may then be arranged with circuits that are capable of connecting with the smart device. Such a smart device may be any smart device capable of receiving and transmitting information. If such a device receives certain information from a medicament delivery device, it may communicate directly to the user. Again, the communication may be done visually, e.g. by text stored in the smart device. Also, the communication may be done audibly, e.g. by a recorded message stored in the smart device and played through loudspeakers of the smart device. In this respect, the smart device may be arranged with a computer program or application that is started when the smart device receives the information from the electronics module of the medicament delivery device.

In this respect, the smart device may be arranged with communication modules that are capable of communicating with wireless networks, such as Wifi-networks, mobile communication networks, etc. such that it may transmit and/or receive information after being activated by the electronics module of the medicament delivery device. For instance, instead of having a program or an application stored in the smart device, the smart device may connect to suitable sites on the internet, where the appropriate information may be presented to the user.

Even though the medicament delivery devices have been described in connection with a medicament container filled with a treatment drug, it is to be understood that the medicament container could be a so called dummy that does not contain any medicament and that can be used for tutorial purposes. It is further to be understood that the communication unit may be integrated in the medicament delivery device, but it may also be arranged as a separate unit that could be connectable to the medicament delivery device; an add-on.

It is to be understood that the embodiments described above and shown in the drawings are to be regarded only as non-limiting examples of the disclosure and that it may be modified in many ways within the scope of the patent claims.

The invention claimed is:

[1. A medicament delivery device comprising:

a housing, which housing is arranged to accommodate a medicament container, a drive mechanism that engages the medicament container when the drive mechanism is activated, where the drive mechanism comprises an actuator having a cut-out located in a distal end wall, a switching element and a force element, where the force element directly engages an inside surface of a distal end of the switching element and where a conductive lead extends through the cut-out, a communication unit operatively connected to the housing and electrically connected to the conductive lead, and a switch comprising a contact surface on the lead that is located inside of the actuator and a conductive surface of the distal end of the switching element, where the switch is in an open position before and partially during activation of the drive mechanism and is in a closed position when the conductive surface of the distal end of the switching element moves axially and distally relative to the actuator coming into contact with the contact surface of the lead, where the communication unit is activated when the switch is closed.]

[2. The medicament delivery device according to claim 1, wherein said force element is a drive spring arranged to act on and move a plunger rod of said drive mechanism in a proximal direction.]

[3. The medicament delivery device according to claim 2, wherein said drive spring is arranged to act on a plunger rod driver of the drive mechanism, such that the plunger rod driver is moved in a proximal direction acting on the switching element at the end of the dose delivery sequence.]

[4. The medicament delivery device according to claim 1, wherein said communication unit is arranged to communicate directly with a user.]

[5. The medicament delivery device according to claim 4, wherein the communication unit provides the user with an audible or visual signal.]

[6. The medicament delivery device according to claim 4, wherein said communication unit is arranged to communicate with wireless networks and/or mobile communication networks, comprising transmitting and receiving data.]

[7. The medicament delivery device according to claim 4, wherein said communication unit is operably connected to a number of sensors in said medicament delivery device.]

[8. The medicament delivery device according to claim 7, wherein said communication unit is arranged to obtain information regarding patient adherence.]

[9. The medicament delivery device according to claim 4, wherein said communication unit comprises a data storage module.]

[10. The medicament delivery device according to claim 4, wherein said communication unit is configured to automatically connect to an emergency call center.]

[11. The medicament delivery device according to claim 10, wherein said communication unit comprises a loudspeaker and a microphone for enabling speech information between user and emergency call center.]

[12. The medicament delivery device according to claim 10, wherein said communication unit further comprises a positioning function, capable of obtaining the geographical position when the switch is activated, and being capable of transmitting said geographical position to the emergency call center.]

[13. The medicament delivery device according to claim 1, wherein the communication unit communicates with a smart device.]

[14. The medicament delivery device according to claim 1, wherein the communication unit is integrated in the medicament delivery device or arranged as a separate unit connectable to the medicament delivery device.]

[15. A medicament delivery device comprising:

a housing;

a drive mechanism positioned with the housing, where the drive mechanism comprises a plunger rod driver, an actuator and an elongated plunger rod having a distally directed end surface, where the plunger rod driver moves axially in a proximal direction relative to the housing;

a switch having a closed position and an open position;

a communication unit operably connected to the housing and in electrical communication with the switch, where the switch activates the communication unit when the switch is in the closed position;

a switching element directly in contact with the distally directed end surface of the elongated plunger rod and having an electrically conductive surface, where the switching element is axially fixed to the plunger rod driver, moves in a proximal direction, and is released from the plunger rod driver when an end of dose delivery sequence is reached causing the switch to move axially in a proximal direction relative to both the housing and the switching element such that the switch moves from the open position to the closed position and the electrically conductive surface of the switching element contacts a corresponding conductive surface on the switch.]

[16. The medicament delivery device of claim 15, where the corresponding conductive surface is in electrical communication with the switch.]

[17. The medicament delivery device of claim 15, further comprising a compression spring which upon activation of the medicament delivery device causes the plunger rod to move proximally.]

*18. A medicament delivery device comprising:*

*a housing;*

*a medicament container axially fixed within the housing;*

*a plunger rod that slidably positioned within and relative to the housing, where the plunger rod engages a slidable stopper within the medicament container during dose delivery;*

*an actuator having a tubular portion located in a distal end of the actuator that surrounds a portion of the plunger rod, a switching element, and drive spring that is in direct contact with the switching element; and*

*a communication unit operatively positioned within the housing and electrically connected to a switch comprising:*

*a contact surface on one end of a conductive lead that extends through a cut-out in a distal end wall of the tubular portion; and*

*a contact element positioned on a flexible tongue that is electrically connected to the communication unit;*

*wherein the switch is in an open position before and partially during dose delivery,*

*wherein the switch moves to a closed position when the drive spring moves the switching element axially and distally relative to the actuator such that the switching element engages with and pushes the flexible tongue causing the contact surface to come into contact with the contact element, and*

*wherein the communication unit is activated when the switch is in the closed position.*

* * * * *